United States Patent
De Paepe et al.

(10) Patent No.: US 10,645,255 B2
(45) Date of Patent: May 5, 2020

(54) SYSTEM AND METHOD FOR ENDOSCOPE CALIBRATION

(71) Applicant: BARCO NV, Kortrijk (BE)

(72) Inventors: Lode De Paepe, Ghent (BE); Guillaume Spalla, La Madeleine (FR); Arnout Vetsuypens, Ostend (BE); Gert Van Hoey, Sint-Amandsberg (BE)

(73) Assignee: BARCO NV, Kortrijk (BE)

( * ) Notice: Subject to any disclaimer, the term of this patent is extended or adjusted under 35 U.S.C. 154(b) by 10 days.

(21) Appl. No.: 16/069,913

(22) PCT Filed: Jan. 13, 2017

(86) PCT No.: PCT/EP2017/050696
§ 371 (c)(1),
(2) Date: Jul. 13, 2018

(87) PCT Pub. No.: WO2017/121866
PCT Pub. Date: Jul. 20, 2017

(65) Prior Publication Data
US 2019/0028614 A1    Jan. 24, 2019

(30) Foreign Application Priority Data

Jan. 15, 2016 (GB) .................................. 1600873.2

(51) Int. Cl.
*G06T 7/80* (2017.01)
*H04N 5/243* (2006.01)
(Continued)

(52) U.S. Cl.
CPC ....... *H04N 1/6055* (2013.01); *A61B 1/00009* (2013.01); *A61B 1/00057* (2013.01);
(Continued)

(58) Field of Classification Search
CPC .............................. H04N 1/6055; G06T 7/80
See application file for complete search history.

(56) References Cited

U.S. PATENT DOCUMENTS 4,827,908 A * 5/1989 Matsuo .............. A61B 1/00059
348/71
6,190,308 B1 * 2/2001 Irion ...................... A61B 1/042
348/188

(Continued)

FOREIGN PATENT DOCUMENTS

| JP | H05137693 A | 6/1993 |
|---|---|---|
| JP | 2005043105 A | 2/2005 |

(Continued)

OTHER PUBLICATIONS

International Search Report in related PCT/EP2017/050696, dated May 9, 2017.

(Continued)

*Primary Examiner* — Irfan Habib
(74) *Attorney, Agent, or Firm* — Bacon & Thomas, PLLC

(57) ABSTRACT

A system and method for calibrating an endoscope having the camera and the light source close to each other in an enclosed environment. The system includes a colour chart plate, being specularly reflecting, having radially extending colour patches, and a circular central achromatic bright field that can handle the automatic gain control of the camera. The colour chart can be mounted into a container unit having mechanically connected holders to support the endoscope arm.

19 Claims, 3 Drawing Sheets

(51) Int. Cl.
  *H04N 9/73*   (2006.01)
  *H04N 1/60*   (2006.01)
  *A61B 1/00*   (2006.01)
  *G01J 3/52*   (2006.01)
  *A61B 1/045*  (2006.01)
  *G06T 7/90*   (2017.01)

(52) U.S. Cl.
  CPC .............. *A61B 1/045* (2013.01); *G01J 3/522* (2013.01); *G01J 3/524* (2013.01); *G06T 7/80* (2017.01); *G06T 7/90* (2017.01); *H04N 1/6008* (2013.01); *H04N 1/6033* (2013.01); *H04N 1/6086* (2013.01); *H04N 5/243* (2013.01); *H04N 9/735* (2013.01); *G06T 2207/10024* (2013.01); *G06T 2207/10068* (2013.01); *G06T 2207/30244* (2013.01); *H04N 2201/3256* (2013.01)

(56) References Cited

U.S. PATENT DOCUMENTS

| | | | | |
|---|---|---|---|---|
| 6,821,245 | B2 * | 11/2004 | Cline | A61B 1/00009 600/160 |
| 7,502,033 | B1 | 3/2009 | Axelrod | |
| 8,382,657 | B1 | 2/2013 | Bodor et al. | |
| 8,553,077 | B2 * | 10/2013 | Ozawa | A61B 1/0638 348/68 |
| 8,564,651 | B2 * | 10/2013 | Ozawa | A61B 1/0638 348/68 |
| 8,624,966 | B2 * | 1/2014 | Ozawa | A61B 1/00057 348/68 |
| 8,665,327 | B2 * | 3/2014 | Ozawa | A61B 1/0638 348/68 |
| 8,758,223 | B1 | 6/2014 | Bodor et al. | |
| 8,858,429 | B2 * | 10/2014 | Mizuyoshi | A61B 1/0653 600/118 |
| 8,937,652 | B2 * | 1/2015 | Ariyoshi | A61B 1/00 348/68 |
| 9,155,457 | B2 * | 10/2015 | Yamashita | A61B 1/0638 |
| 9,621,781 | B2 * | 4/2017 | On | G02B 7/36 |
| 2002/0016620 | A1 * | 2/2002 | Tsujita | A61N 1/08 607/88 |
| 2005/0024658 | A1 * | 2/2005 | Ota | H04N 1/6055 358/1.9 |
| 2007/0142707 | A1 * | 6/2007 | Wiklof | A61B 1/00096 600/118 |
| 2007/0211274 | A1 * | 9/2007 | Donomae | H04N 1/60 358/1.9 |
| 2007/0282169 | A1 * | 12/2007 | Tsujita | A61B 1/00016 600/160 |
| 2009/0062617 | A1 * | 3/2009 | Mizuyoshi | A61B 1/0638 600/178 |
| 2009/0167149 | A1 * | 7/2009 | Ito | A61B 1/0638 313/501 |
| 2011/0034770 | A1 * | 2/2011 | Endo | A61B 1/0638 600/118 |
| 2012/0078046 | A1 * | 3/2012 | Sasaki | A61B 1/00009 600/109 |
| 2012/0253122 | A1 * | 10/2012 | Minetoma | A61B 1/00057 600/109 |
| 2016/0073076 | A1 * | 3/2016 | Carroll | H04N 5/217 348/242 |

FOREIGN PATENT DOCUMENTS

| | | | |
|---|---|---|---|
| JP | 2010088559 | * | 4/2010 |
| JP | 2010088559 A | | 4/2010 |

OTHER PUBLICATIONS

Written Opinion in related PCT/EP2017/050696, dated May 9, 2017.
International Preliminary Report on Patentability in related PCT/EP2017/050696, dated May 23, 2018.
HTTP:///www.image-engineering.de/products/solutions/starter-kits/637-starter-kit-medical-endoscopy and http://www.image-engineering.de/products/charts/all/516-te188, Image Engineering, pp. 1-2, (Accessed Oct. 1, 2018).
HTTP:///dsclabs.com/dsc-products/law-enforcement-medical/the-medicol-chart/, DSC Labs, pp. 1-3, Dec. 21, 2015.
HTTPS://shop.visuals.ch/en/test-chart-clap/79823-image-engineering-etc-te132-d-te132-iso-test-pattern-no-2-transparent.html, TE132—TE132 ISO test pattern No. 2 (1-18LP/mm—sheet with 12 patterns) chart size D35, Image Engineering, pp. 1-2, (Accessed Oct. 1, 2018).
HTTPS://www.image-engineering.de/products/charts/all/561-te240, HTTPTE240—TE240 ISO 21550 dynamic range chart size D35 (available with max. density 4.0 or 6.0), Image Engineering, pp. 1-3, (Accessed Oct. 1, 2018).
HTTPS://polynton.ca/notes/color/GretagMacbeth-ColorChecker.html, ColorChecker ("Macbeth"), pp. 1-2, (Sep. 11, 2008).
HTTPS://www.image-engineering.de/products/charts/all/575-te258, IT8 target, Image Engineering, pp. 1-3, (Accessed Oct. 1, 2018).
HTTPS://www.image-engineering.de/products/charts/all/516-te188, TE188—TE188 color rendition chart size D35 (X-Rite ColorChecker), Image Engineering, pp. 1-3, (Accessed Oct. 1, 2018).
HTTPS://www.image-engineering.de/products/charts/all/568-te250, TE250—USAF 1951 target chart size D35, Image Engineering, pp. 1-3, (Accessed Oct. 1, 2018).
European Office Action in corresponding European Application No. 17702299.3-1124, dated May 20, 2019.

* cited by examiner

SYSTEM AND METHOD FOR ENDOSCOPE CALIBRATION

The present invention relates to methods and systems for calibrating endoscopes.

BACKGROUND OF THE INVENTION

Calibration of camera systems can be made by having a camera system acquiring an image of a colour chart, and comparing the obtained values for the different patches to known reference values in a specified colour space, for instance standard RGB. A calibration algorithm calculates a transform in order to reduce the errors between the acquired values for the patches and the reference values. This transformation results in corrected colours from the camera for the specified colour space.

Colour charts have traditionally been rectangular having several square or rectangular patches. The colours of the patches are carefully selected so that they cover the gamut of the specified colour space, and in specific cases, colours that are regularly present in the images are also added to the chart to increase precision of the calibration. For instance, the colour chart in FIG. 1 is optimized for medical applications (http://dsclabs.com/dsc-products/law-enforcement-medical/the-medicol-chart/). The chart includes 32 precision colour chips providing an expanded colour gamut said to be specially designed for the medical imaging community. A nine step grayscale is said to provide a neutral, dynamic range reference. DSC CamWhite on the rear is said to provide a spectrophotometrically neutral white reference for quick white balancing.

For instance also, the colour chart TE188 from Image Engineering like in FIG. 1 is optimized for medical applications (http://www.image-engineering.de/products/solutions/starter-kits/637-starter-kit-medical-endoscopy and http://www.image-engineering.de/products/charts/all/516-te188). The chart includes 18 precision colour chips providing an expanded colour gamut said to be specially designed for the medical imaging community. A 6 step grayscale can provide a neutral, dynamic range reference.

TE132—TE132 ISO test pattern No. 2 (1-18 LP/mm—sheet with 12 patterns) chart size D35
TE188—TE188 color rendition chart size D35 (X-Rite ColorChecker)
TE240—TE240 ISO 21550 dynamic range chart size D35 (available with max. density 4.0 or 6.0)
TE250—USAF 1951 target chart size D35

These types of colour charts may not be suitable for camera systems with an integrated light source that are used to inspect enclosed spaces, such as endoscopes. Endoscopes can for example be used in healthcare applications or to inspect machines or engines, or to inspect building constructions. There are several hurdles to overcome when calibrating an endoscope:

a. Most endoscopes have a built-in automatic gain control system to optimize the image performance under the very different lighting conditions inside the structure to be inspected. Depending on the distance of the camera and its built-in illumination to the environment, the image can become darker or lighter. To compensate this, the camera changes automatically its gain to have always a bright image. Automatic gain control algorithms are based on increasing gain until a certain number of pixels are saturated and clipped. This has an influence on how colours are acquired by the camera system. If the camera saturates at a certain colour, the reproduction of that colour (and possibly others depending of it) will be incorrect. Conventional colour charts do not take into account automatic gain control algorithms of cameras.

b. An effect of a built-in light source is that the image illumination is non-uniform and can resemble a torch, i.e. the centre of the viewing field is very bright and at the edges the image are covered in shadow. The result can be that with conventional colour charts the illumination of the centre patches differs from that of the patches towards the edge. This has a big influence on how the colour patches at different locations are acquired by the camera. Thus, a conventional rectangular colour chart is not suitable for colour calibration of systems with a built-in light source.

c. The calibration process can depend on knowledge of the coordinates of the different patches. Thus, it is important to know the relation between the camera pixels and the coordinates of the colour chart, so the camera needs to be aligned with the colour chart. With a conventional camera system, the housing and field of view of the camera is often rectangular so it is intuitive to align the camera with a rectangular colour chart. The field of view of an endoscope is also rectangular but the image is clipped to a circular shape by the optical system. So in case of the typical round tube and small endoscope housing, or in the case of the glass fibre, the natural approach to alignment by selecting a rectangular shape is lost. Thus, it is difficult to align an endoscope system to a conventional colour chart.

d. Alternatively, the position of a patch can be automatically detected, e.g. by recognizing the rectangular shape of the patch, but also by comparing the acquired values of the patch to the reference values to define the orientation of the colour chart. To be really certain that a patch corresponds with a reference value, the image has to be calibrated. But to calibrate the image, the patches need to be extracted first. Thus, this alternative method is not solving the problem of alignment.

e. An endoscope camera is normally not directly inserted inside the structure to be inspected. A tube or glass fibre with a lens is connected to the camera of the endoscope and this tube or fibre is inserted in the structure to be inspected. This optical path is not perfect. For example, crosstalk inside the tube results in light structures next to the patches that are creating a light shadow border inside the patch. This has an effect on the final calibration because the error between the acquired values and the reference values is artificially increased. Conventional colour charts do not consider this cross talk.

f. Colour charts are available in a large number of varieties but also in numbered versions. Many colour calibration algorithms support the use of different colour charts. The chart is either manually selected or automatically detected based on the acquired values of the patches. For automatic detection, it is assumed that the used chart is the one with the reference values for the patches being the closest to the acquired values. In either case there is a risk that the wrong colour chart is selected, which would lead to incorrect calibration results.

During calibration it is also desirable to have the colour chart and camera uptake shielded from ambient light in order to mimic the environment during endoscope operation.

SUMMARY OF THE INVENTION

In one embodiment of the invention there is a system provided for colour calibration comprising an endoscope having an image capturing device such as a camera and a light source, a container unit with holders and a circular colour chart plate, wherein the colour chart plate has a mainly specularly reflective surface facing the camera, and radial colour patches with the same radial extension, a circular central achromatic bright field with a radius between 30-70% of the radial extension of a colour patch, and the circular central achromatic bright field has at least the brightness of the brightest colour patch in the colour chart. The circular central achromatic bright field could be white.

The circular central achromatic bright field can be used to manage the automatic gain control so that the signal from the colour patches outside the circular central achromatic bright field is not saturated.

The colour chart plate may have a transparent and/or smooth surface facing the camera, for example may be made of glass or quartz.

This protects the colour chart from wear and also makes it easy to keep it clean, which can be especially important for medical applications.

The colour patches and/or the circular central achromatic bright field can have a black contour or border that will avoid having light artefacts inside the patches or the white field e.g. due to camera brightness compensation to enhance contrast.

The area around the colour patches and the circular central achromatic bright field can be white. This can compensate for possible decrease in illumination towards the camera field of view boundaries, which can arise with endoscope light sources.

The outer shape of the colour chart plate can be rectangular or circular or any combination thereof.

The area of the circular central bright achromatic field can be excluded from being used as a reference for colour calibration. This will avoid the use of saturated colour reference values for the calibration. Additionally, central strong reflection of the light source can be kept from disturbing the colour patch readings.

The colour chart plate can have unsymmetrical markings and/or unsymmetrically placed markings. Thus if the markings are unsymmetrical, they can be symmetrically or unsymmetrically placed. If the markings are symmetrical they should be unsymmetrically placed. If automatic reading of the colour patches is used, these markings can be used to obtain the orientation of the chart.

The colour chart can further comprise a marking code for identification, e.g. a QR code. The code can store relevant information of the colour chart, e.g. type of chart, but also user specific information. Generally, the QR code could also comprise updates and upgrades for the endoscope system, e.g. by using Java.

The container unit can comprise a replaceable colour chart plate.

A colour chart plate related to each measurement procedure and/or user can be placed inside the container unit.

The container unit can have at least one opening to receive the endoscope arm.

The container unit can have at least two holders which each in turn can have at least one notch or groove. The holders can be rotatable to each other, and/or the holders and the container can be rotatable relative to each other.

The holders will maintain the endoscope arm in a correct position. The notches or grooves will further stabilize the arm position during operation.

The inner walls of the container can be covered with a light absorbing material and/or structures for light scattering. This will reduce the specular reflection inside the container.

In another embodiment of the invention there is a method provided for calibrating an endoscope image capturing device such as a camera comprising an endoscope with a light source and an image capturing device such as a camera having pixels, a container, and a colour chart plate with a colour chart having a circular central achromatic bright field, the method comprising the steps of inserting the endoscope into the container, aligning the camera's field of view with the circular central achromatic bright field of the colour chart and adjusting the size of the beam until pixels inside the circular central achromatic bright field are saturated while pixels outside the circular central bright achromatic field are not saturated, extract colour values from the colour patches and calculate correction values.

By letting the camera saturate in the circular central achromatic bright field, the signal from the colour patches is still unsaturated so that a correct calibration can be performed.

The method can further comprise reading markings on the colour chart plate to define its orientation. This can be used if automatic reading is implemented.

The method can further comprise that colour values of each patch are extracted and compared to reference values, and the differences between the extracted values and the reference values are implemented in a correction function that is applied to the output signal.

The method can further comprise calculating at least one user preference correction relative the colour chart, using a second set of patches or an image.

If this personalized calibration is made on top of a calibration using a first known colour chart, the personalized calibration can be directly applied to any endoscope system that has been calibrated with the first known colour chart, and obtain the same outcome.

The method can further comprise storing each of the at least one correction values in a look-up table that is stored locally or remotely in a non-volatile memory. By using a ready correction table stored in a non-volatile memory the endoscope can be fast and consistently set up.

The method can further comprise having the endoscope acquiring an image or a video stream of a structure, and applying the correction values of the at least one look-up table onto the image or video stream. In this way the image or video stream will be calibrated according to the chosen references.

The method can further comprise using an ICC (International Color Consortium) profile to adapt the calibrated stream to a specific display.

By using the display's ICC profile, the stream can be further optimized for that specific display.

The method can further comprise excluding using the circular central bright achromatic field as reference for colour calibration. In this way the camera can be kept from using saturated colour reference values for the calibration. Additionally, the central strong reflection of the light source can be kept from disturbing the colour patch readings.

DETAILED DESCRIPTION OF THE INVENTION

A method and system have been developed that can remove one or more of the above mentioned deficiencies and make sure the colour reproduction during calibration is satisfactory or optimal.

Figure 1:
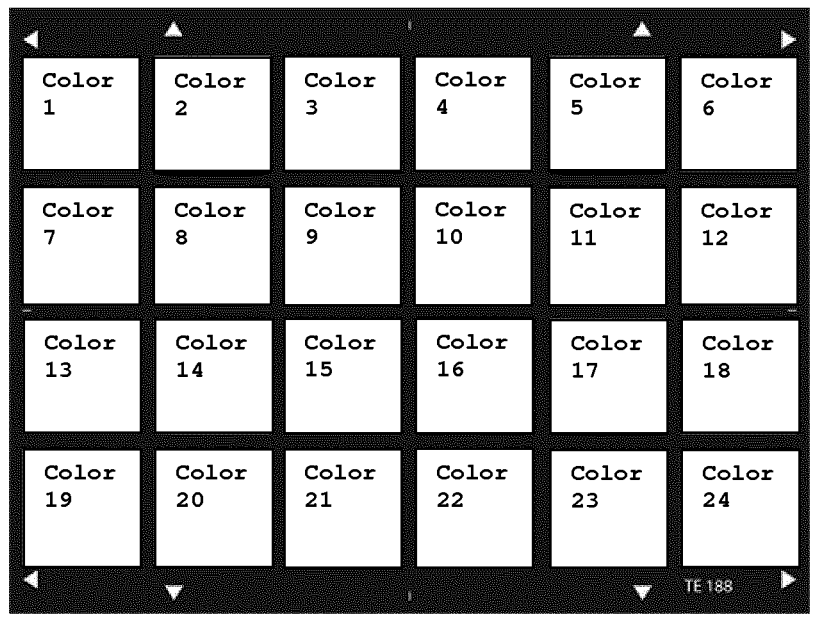
FIG. 1 shows an example of a conventional colour chart.
Figure 2:
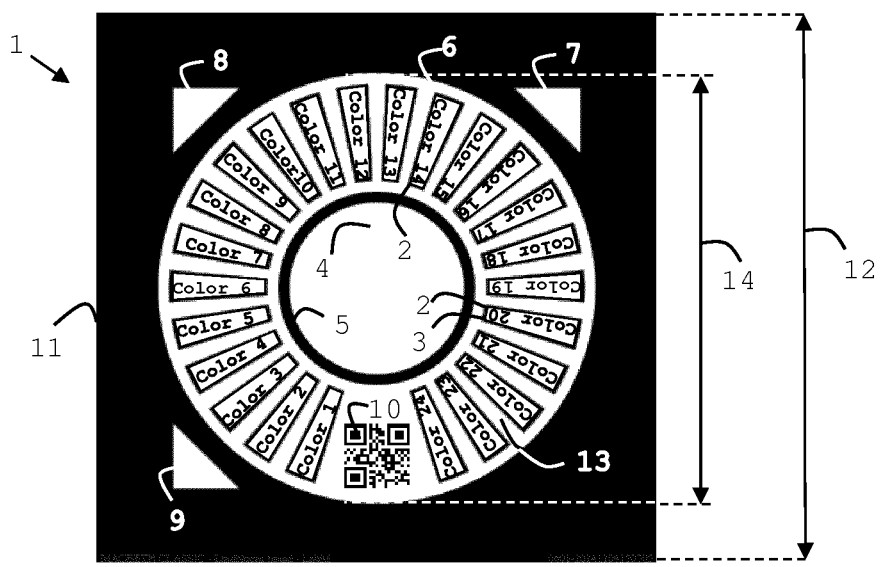
FIG. 2 shows an embodiment of the present invention comprising a colour chart plate.

FIG. 2 shows an embodiment of the present invention comprising a colour chart plate 1 of side 12, having a circular colour chart 13 of diameter 14, which comprises a multiple of colour patches 2. Optionally, the circular colour chart 13 has a circular central achromatic bright field 4, which is bright and achromatic, in the form of a circle for example, optionally surrounded by a black border 5 which has the same shape as the outer shape of the circular central achromatic bright field 4. The colour patches are shown as spaced truncated triangles or truncated sectors of a circle. Each colour patch 2 is optionally surrounded by a black border 3 and the colour patches 2 are extending radially like a sector of a circle between the circular central achromatic bright field 4 and the rim of the colour chart 13. Between the patches 2 there is a white field 6 and there is also an identification code such as a barcode or QR (Quick Response) code 10. Outside the circular patch area there is a black area 11 comprising three white arrows 7, 8 and 9. The reference values for the colour patches can be made by using values from existing charts, such as e.g. IT8 target or MacBeth Color Checker, but values from any colour chart of choice can be used.

The circular central achromatic bright field 4 in the centre of the chart 1 can be used to manage the automatic gain control. The light source can be pointed towards the centre of the colour chart plate 1 and to be incident thereon perpendicularly. The circular central achromatic bright field 4, which is located closest to the light source, will receive the highest amount of the illumination.

Therefore camera pixels viewing the circular central achromatic bright field 4 can become saturated before camera pixels that are viewing outside the circular central achromatic bright field 4, and clipped by the automatic gain control algorithm. In this way, saturation of the camera pixels viewing the surrounding colour patches 2 can be avoided since they will receive less illumination than pixels viewing the circular central achromatic bright field 4. Further, the illumination can be applied perpendicular to the colour chart plate 1 so that reflection of the light source will return within in the envelope of the circular central achromatic bright field 4 and will not disturb the colour correction process. This becomes more important with an increased specular reflection of the circular central achromatic bright field 4. The border 5 can aid in positioning and sizing (manually or automatically) the illuminating light beam. The inventors have found that for a preferred embodiment, the diameter of the circular central achromatic bright field 4 can be 30-70% of the outer diameter of the colour patches. The U.S. Pat. No. 7,502,033 discloses a colour chart having an achromatic central field where the diameter of the central field is much smaller than 30% of the outer diameter of the colour patches. To make sure that the central achromatic bright field 4 can make the camera saturate before the colour patches, it can be advantageous to use a colour or tone that gives higher luminance than any of the colour patches. For example, if the colour patches comprises white, the same white can be used for the central achromatic field. In general, the central achromatic bright field 4 could have at least the brightness of the brightest colour patch of its colour chart.

The truncated sector arrangement of colour patches can avoid problems of non-uniform illumination. If the light declines towards the outer parts of the camera field of view, the effect will be similar for each patch. The white background 6 also helps to compensate for the decrease of light towards the boundaries.

The truncated sector arrangement of colour patches can facilitate the alignment of the camera field of view to the colour chart since all colour patches are extending in the same way relative to the centre of the colour chart. Although in FIG. 2 all the truncated sectors 2 are the same size this is not a limitation of the present invention. It is possible to have different widths of the truncated sectors 2). Thus, if the camera is pointing towards the centre of the circular central achromatic bright field 4 (and the zoom is correctly adjusted) all colour patches 2 can be acquired in a similar way. In the case where the extraction of the colour levels of the patches 2 is automatic, the camera can also record the markings 7, 8 and 9. If the three markings are included in the camera shot, it is possible to determine how the colour chart is oriented. In FIG. 2 three white triangles 7, 8 and 9 are used, but the markings could be of any number, shape, colour, or layout, as long as the outcome indicates the unique orientation of the colour chart.

The borders 3 around each patch 2 can reduce the artefacts between the patches 2 put next to a lighter or white background. Such an artefact can arise from camera adjustments at the interface between two colours. If a camera is looking at a lighter and a darker field put next to each other so that they have a common interface, it can happen that the camera tries to increase contrast by e.g. increasing the luminance of the darker field. In the case of a colour patch 2 next to a white background, this can result in bands of lighter colour (increased luminance) in the colour patch. This will in turn increase the error between the acquired value of the patch and the corresponding reference value and hence give rise to an incorrect calibration. By adding the black border 3, a coloured patch 2 will be the lighter of the fields and the increase in luminance will happen in the black border 3. If there is a tube connecting the lens and the camera, the black border 3 also reduces crosstalk inside the tube that could result in light shadows inside the colour patch.

In order to facilitate the (automatic) extraction of the patches, an identification marking such as a QR (Quick Response) code 10 can be added to the colour chart, containing related information, for example the type and version of the colour chart. Also additional information could be added to the QR code, like for instance an identification of the user of the colour chart. This ID could be used to further adjust the calibration correction to user specific preferences for the colour chart in question. Since the user specific preferences will always originate from that colour chart, they can be applied to fine tune the calibration on any endoscope system.

In one embodiment of the present invention, the colour chart plate 1 has a surface facing the camera which is specularly reflecting. This can for example be implemented with a protective cover of a material with a transparent smooth and rigid surface, such as for example clear glass or quartz. The cover glass will increase the durability of the colour chart and make sure the colour patches are correct also after a long time in use. Further, in the field of medical endoscopy, such a surface is easy to wipe off and sterilise. Such surfaces of this type mostly contribute to an increased specular reflection. While most surfaces comprise both specular and diffuse reflection, it is hereby meant that a specularly reflecting surface has a majority of specular reflection. Though the reflection of a diffusively reflecting surface has a limited intensity, it will be present over a large view angle, for example will return to the camera together with the colour filtered light from a colour patch. A smooth plane surface, e.g. such as clear glass, will have an intense specular reflection, but over a limited view angle and the impact of reflection returning to the camera can therefore be better controlled and limited. The present invention can exclude the use of the circular central bright achromatic field as colour reference so that the intense central reflection is not influencing the calibration. Application JP2010088559 describes a radial colour chart but it is desirably composed of a matte material, aiming to prevent overexposure by reflected light.

In addition, to make sure the calibration environment corresponds with the actual conditions during acquisition, it has to be considered that the endoscope can be operated with practically no ambient light. Therefore it would be advantageous if the endoscope camera could be shielded as much as possible from ambient light during calibration. One solution is to perform the calibration in a dark room. Another solution is to enclose the colour chart in some type of container.

U.S. Pat. No. 8,624,966 B2 describes a cylindrical container for calibrating endoscopes, where a colour chart can be placed on the bottom of the cylinder. However, there is no real fixation of the arm that is inserted into the box, and it can allow rotations with three degrees of freedom around its fixation point, during a calibration procedure or between two procedures. These rotations are uncontrolled and could not be used for an endoscope having an inclined lens. Further, there are no measures taken to prevent internal reflections inside the cylinder. Being a medical endoscope, the box would also need to be sterilized for each re-calibration during the procedure since the endoscope is touching the lid of the container.

Figure 3:
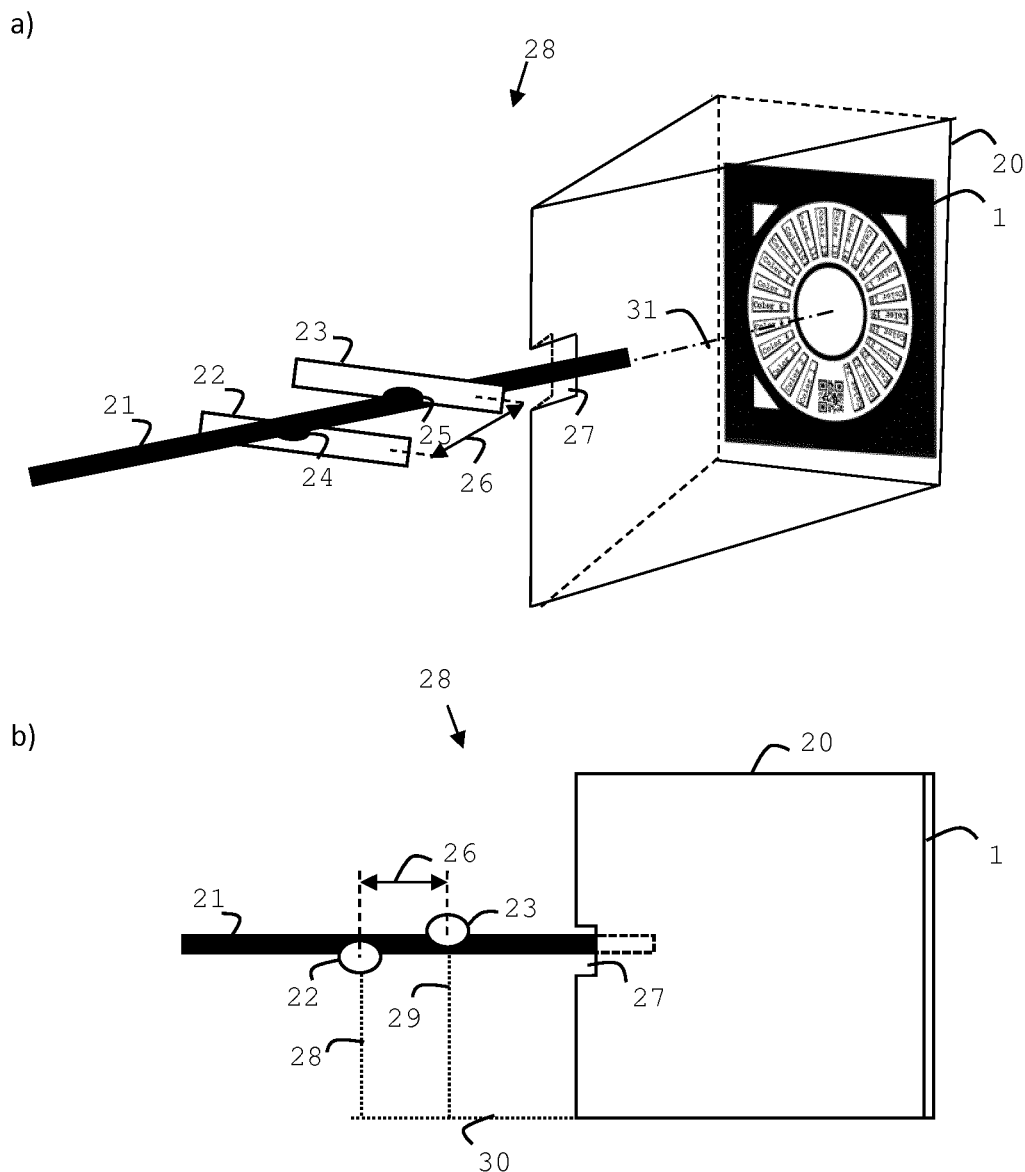
FIGS. 3 a) and b) show an embodiment of the present invention comprising a colour chart plate, a container and holders.

FIG. 3a) shows an embodiment of the present invention where a container unit 28 comprises a container 20 that provides an enclosed space (apart from the opening 27) and holders 22 and 23. In FIG. 3a) the walls of 20 are shown as transparent for clarity. The inner side walls of 20 can be marked or covered, e.g. painted, with an absorbing dark material such as a black paint. They can also be provided with a structure, in order to reduce internal specular reflections. The endoscope arm 21 enters the container 20 via the opening 27 and points towards the centre of the colour chart plate 1 placed at the rear end of the container 20. In case of medical applications, the opening 27 can be made larger than the arm 21 so that no part of the container has to touch the arm 21. In order to fix the position of the arm 21, there are provided holders 22 and 23 separated with a distance 26. Each holder can have at least one notch or groove, 24 and 25 respectively, that can be facing towards the arm 21. In this way they can hold the arm 21 in a fixed position so that the angle between the arm 21 and the normal 31 of the colour chart surface is kept constant. The arm 21 could, or need not, be allowed to rotate around its own axis in the holders 22 and 23. FIG. 3b) shows a side view of the embodiment of FIG. 3a). The holders 22 and 23 can be kept in place by arbitrary means 28 and 29. An arbitrary connection 30 between the holders 22 and 23 and the container 20, can keep the distance and orientation between the holders and the container constant. Members 28-30 are omitted in FIG. 3a) for clarity.

If an endoscope arm with an angled lens, e.g. 30 degrees, is used, there can be a multiple of notches foreseen in the holders 22 and 23. By choosing a notches from the holders 22 and 23 that are not directly in front of each other, the desired angle between the arm 21 and the normal 31 can be reached and the camera will still be looking at the colour chart without inclination (or, alternatively with a chosen inclination). In another embodiment the holders 22 and 23 and the container 20 could be rotated relative to each other until the desired angle between 21 and 31 is reached.

In the case of a medical application it is beneficial to have the holders 22 and 23 accessible outside the container 20 so that it is easy to wrap sterile tissues around them during a procedure.

In one exemplary embodiment, the colour chart in FIG. 2 would have a side 12 of about 10 cm. The other measures of the colour chart are to scale relative to the side 12.

It is preferable to keep the calibration objective and consistent, for example for different points in time and/or for different users and/or for different display monitors.

The colours of the colour charts can be selected depending on the application. In many cases care should be with respect to properties of the displays to be used during the procedure. For example it can be desirable to use the whole gamut of the display. If a user performs a manual calibration, only the colours can be calibrated that are currently visible at the screen. If there is a need to make a new calibration at a later time there might be another collection of colours available. In the case multiple monitors are used, each monitor also needs to be adjusted. If there is a change of user, the new user will most probably make a new calibration depending on historical subjective experience and perhaps the colours available on the display by then.

Figure 4:
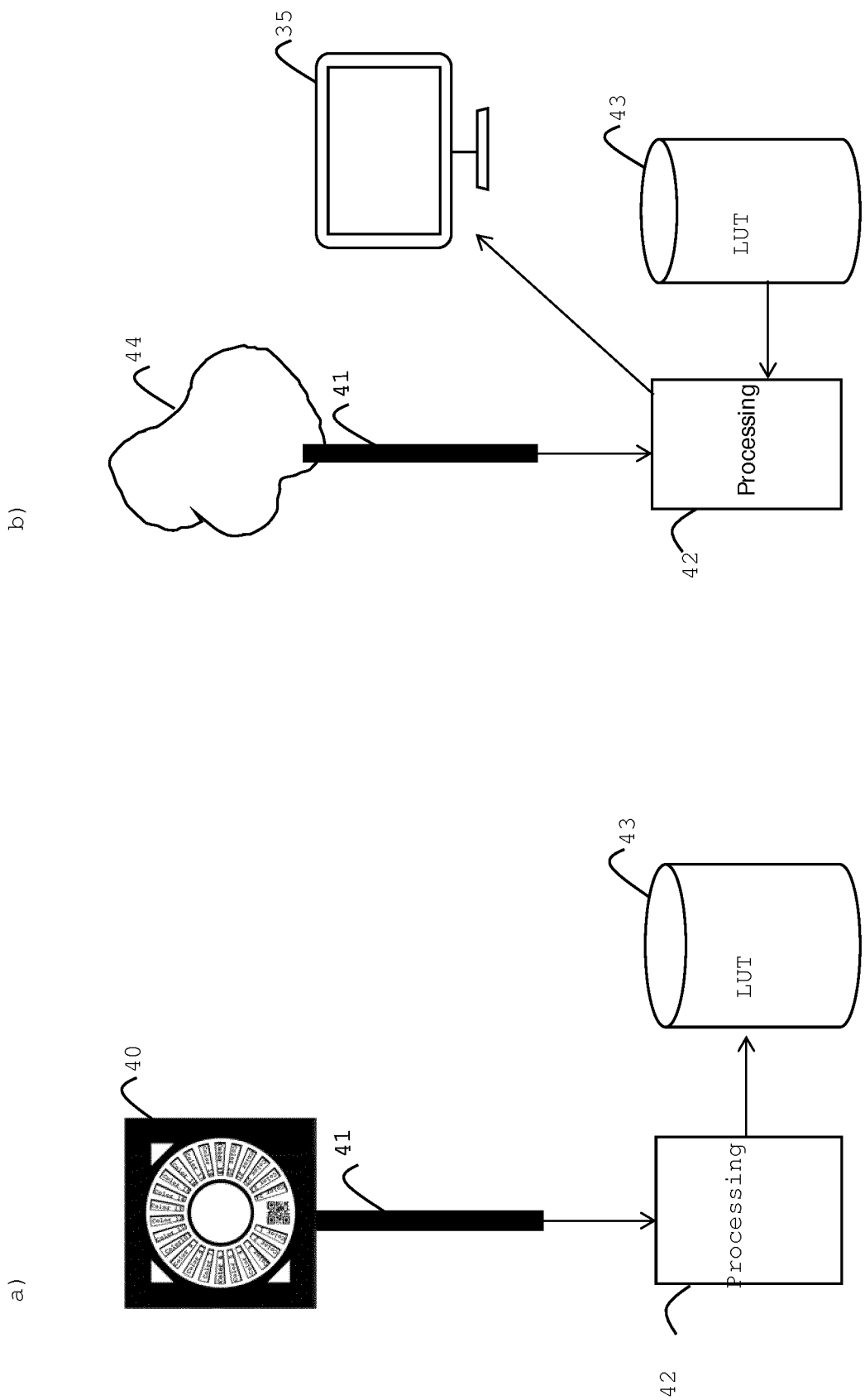
FIG. 4 shows an embodiment of the present invention comprising a system for using LUTs.

In one embodiment of the present invention the correction values can be stored in look-up tables, LUTs. FIG. 4a) shows an embodiment where the endoscope 41 can be calibrated with the colour chart 40. The acquired image is sent to an available processing unit 42, for example a personal computer on-site or processing power provided remotely, e.g. by a remote cloud service. The processing unit 42 extracts the colour values from the acquired image, calculates the corrections and arranges the values in an LUT. The LUT is sent to a central database 43 that can be located on-site or remotely e.g. in a remote cloud service. FIG. 4b) shows how the endoscope 41 is used to investigate a structure 44. The image or stream of images is sent to the processing unit 42 where the LUT is obtained from the database 43 and applied in real-time, by software, to the image or stream of images and the result is sent to the display 35. Alternatively the LUT can be applied by dedicated hardware (e.g. ASIC, FPGA, GPU, . . . ) in the video path.

In the following, an exemplary embodiment of how the invention can be used in a calibration procedure is described. Reference can be made to FIGS. 3a), 3b) and 4a) and 4b).

1. The endoscope (arm) is inserted in the box with the colour chart. The position of the box and the endoscope is adjusted until the field of view of the camera (shielded to a circular shape) is aligned with the colour chart. The endoscope is switched on.

2. The image acquired by the endoscope is visible on a display. The colour calibration system indicates on screen if all parameters for a successful calibration are fulfilled. These parameters can be for instance the position of the endoscope, the zoom level, the focus of the endoscope, the amount of light, . . . . This step makes sure that a user performs a calibration in proper conditions (to avoid that he only afterwards would be notified that the calibration was not successful because e.g. the image is to blurred to recognize the colour chart).

3. When the parameters for a successful calibration are fulfilled, the actual calibration can be initiated. The initiation can be automatic or manual. The system detects the position of the patches based on the position of markings on the colour chart (e.g. triangles as in FIG. 2) and if an identification mark such as a barcode or a QR code is present, it reads the information therein, e.g. the type of colour chart. If no identification mark such as a barcode or QR code is present, the system can recognize the type of the chart based on the acquired colour values. The definition of the chart is coupled automatically by the calibration system to the type of the colour chart. The type of the colour chart can also be selected manually.

4. The calibration system takes one image of the full colour chart and extracts the colour values for the different patches. The acquired values are compared to the reference values of the colour chart. The reference values are part of the definition of the colour chart and are valid in a certain reference colour space, for example L*a*b or sRGB, or any other colour space.

5. The calibration system calculates a correction to reduce the error between the acquired colour values for the patches and the reference values, using any arbitrary numerical method.

6. The correction is saved in a suitable non-volatile memory such as in a LUT which can then be applied on a video stream during the endoscopy procedure. The colour representation of the endoscope is now consistent in the reference colour space selected and can be objectively repeated in that colour space. The colours of the colour chart can be chosen to cover the full gamut of a certain display.

7. The user can further adjust the colour appearance of another set of patches to his own preference, for instance by controlling some test objects, until they appear on screen like how he wants them. The procedure is then the same as in 5 and the new correction is saved in a second LUT.

8. The patches used for the determination of the preferences of the user are defined in the reference colour space. This assures that the preferences of the user are valid for every calibrated endoscope and that the second LUT with the preferences only has to be determined once and can be applied after calibration for every calibrated endoscope.

9. Alternatively, the correction for the preferences can also be determined by showing to the user example images instead of the second set of colour patches. The choices made by the user are translated by the calibration software to a correction of the colours and saved in the second LUT.

10. The second LUT is applied to the already calibrated video stream of the endoscope. The user can also decide to load a previously determined LUT with preferences or to load no LUT at all. The second LUT could also be loaded automatically from a storage (local or on a network location) based on an ID that is for instance integrated in the QR code of the colour chart. A user could then use his personalized colour chart to calibrate whatever endoscope and to also have his preferences applied automatically.

11. The calibration system can further adjust the calibrated video stream of the endoscope to the gamut of the display. This is based on ICC (International Color Consortium) profiles. The colour behaviour of a display is described by its corresponding profile and the colour calibration system will apply an additional transformation so that the calibrated video stream is correctly reproduced on different displays.

When no ICC profiles are available, the colour calibration system can output a stream for a known colour space, as for instance sRGB.

The invention claimed is:

1. A method for calibrating a camera system with an integrated light source, the system comprising a camera with the light source, a container, and a colour chart plate with a colour chart having a circular central bright achromatic field, the method comprising steps of:
    inserting the camera into the container,
    aligning the camera's field of view with the circular central achromatic bright field of the colour chart and adjusting a size of a beam from the light source until pixels inside the circular central achromatic field are saturated while pixels outside the circular central achromatic field are not saturated, extract colour values from colour patches and calculate correction values,
    further comprising managing automatic gain control so that the signal from the colour patches outside the circular central achromatic bright field is not saturated,
    wherein the colour values of each patch are extracted and compared to reference values, and the differences between the extracted values and the reference values are implemented in a correction function.

2. The method according to claim 1 comprising reading markings on the colour chart plate to define its orientation.

3. The method according to claim 1 comprising calculating at least one user preference correction relative the colour chart, using a second set of patches or an image.

4. The method according to claim 1 comprising storing information related to the colour chart in a marking or code for identification, for example a quick response code.

5. The method according to claim 1 comprising storing each of the at least one correction values in a look-up table that is stored locally or remotely, in a non-volatile memory.

6. The method according to claim 1 comprising having the endoscope acquiring an image or a video stream of a structure and applying the correction values of the at least one look-up table onto the image or video stream.

7. The method according to claim 1 comprising using an ICC profile or a standard profile, to adapt the calibrated stream to a specific display.

8. The method according to claim 7 wherein the profile is sRGB.

9. The method according claim 1 comprising excluding using the circular central achromatic bright field as a colour calibration reference.

10. A method for calibrating an endoscope camera comprising an endoscope with a light source and a camera, a container, and a colour chart plate with a colour chart having a circular central bright achromatic field, the method comprising the steps of inserting the endoscope into the container, aligning the camera's field of view with the circular central achromatic bright field of the colour chart and adjusting the size of a beam of the light source until pixels inside the circular central achromatic field are saturated while pixels outside the circular central achromatic field are not saturated, extract colour values from the colour patches and calculate correction values, further comprising managing automatic gain control so that the signal from the colour patches outside the circular central achromatic bright field is not saturated wherein the colour values of each patch are extracted and compared to reference values, and the differences between the extracted values and the reference values are implemented in a correction function.

11. The method according to claim 10 comprising reading markings on the colour chart plate to define its orientation.

12. The method according to claim 10 comprising calculating at least one user preference correction relative the colour chart, using a second set of patches or an image.

13. The method according to claim 10 comprising storing information related to the colour chart in a marking or code for identification, for example a quick response code.

14. The method according to claim 10 comprising storing each of the at least one correction values in a look-up table that is stored locally or remotely, in a non-volatile memory.

15. The method according to claim 10 comprising having the endoscope acquiring an image or a video stream of a structure and applying the correction values of the at least one look-up table onto the image or video stream.

16. The method according to claim 10 comprising using an ICC profile or a standard profile, to adapt the calibrated stream to a specific display.

17. The method according to claim 16 wherein the profile is sRGB.

18. The method according to claim 10 comprising excluding using the circular central achromatic bright field as a colour calibration reference.

19. The method according to claim 1, wherein the circular central bright achromatic field is white.

\* \* \* \* \*